(12) United States Patent
Ogawa et al.

(10) Patent No.: US 8,927,286 B2
(45) Date of Patent: Jan. 6, 2015

(54) METHOD FOR PRODUCING CLONE SEEDLINGS

(75) Inventors: Kenichi Ogawa, Kyoto (JP); Etsuko Matsunaga, Tokyo (JP); Naoki Negishi, Tokyo (JP); Masatoshi Ohishi, Tokyo (JP); Humiki Kawai, Tokyo (JP); Toshiaki Tanabe, Tokyo (JP); Akiyoshi Kawaoka, Tokyo (JP)

(73) Assignee: Okayama Prefecture, Okayama (JP)

( * ) Notice: Subject to any disclaimer, the term of this patent is extended or adjusted under 35 U.S.C. 154(b) by 86 days.

(21) Appl. No.: 13/514,402

(22) PCT Filed: Dec. 9, 2010

(86) PCT No.: PCT/JP2010/072137
§ 371 (c)(1),
(2), (4) Date: Jun. 7, 2012

(87) PCT Pub. No.: WO2011/071114
PCT Pub. Date: Jun. 16, 2011

(65) Prior Publication Data
US 2012/0240462 A1    Sep. 27, 2012

(30) Foreign Application Priority Data

Dec. 10, 2009 (JP) ................................ 2009-280017
Dec. 10, 2009 (JP) ................................ 2009-280018

(51) Int. Cl.
| | |
|---|---|
| *C12N 5/00* | (2006.01) |
| *A01G 1/00* | (2006.01) |
| *A01G 7/00* | (2006.01) |
| *A01H 4/00* | (2006.01) |

(52) U.S. Cl.
CPC .. *A01G 1/00* (2013.01); *A01G 7/00* (2013.01); *A01H 4/005* (2013.01)
USPC ........................................... 435/420; 47/58.1

(58) Field of Classification Search
USPC ........................................... 435/420; 47/58.1
See application file for complete search history.

(56) References Cited

U.S. PATENT DOCUMENTS

| | | | |
|---|---|---|---|
| 5,211,738 A | 5/1993 | Sasaki et al. |
| 5,643,853 A | 7/1997 | Morre |
| 5,883,048 A | 3/1999 | Morre |
| 2003/0110527 A1 | 6/2003 | Ogawa et al. |
| 2009/0099023 A1 | 4/2009 | Ogawa et al. |
| 2010/0016166 A1 | 1/2010 | Ogawa et al. |

FOREIGN PATENT DOCUMENTS

| | | |
|---|---|---|
| JP | H6-199611 | 7/1994 |
| JP | 8-228621 A | 9/1996 |
| JP | 11-501034 A | 1/1999 |
| JP | 2001-346464 A | 12/2001 |
| JP | 2004-267044 A | 9/2004 |
| JP | 2004-352679 A | 12/2004 |
| JP | 2005-110506 A | 4/2005 |
| JP | 2006-141252 A | 6/2006 |
| JP | 2008-120815 A | 5/2008 |
| WO | 2008/072602 | 6/2008 |

OTHER PUBLICATIONS

Tyburski et al. Ascrobate-Glutathione Pathway and stress Tolerance in Plants Chapter 2. (Eds.) N. A. Anjum; S. Umar; M.-T Chan 2010. pp. 55-90.*
Le Roux et al. Micropropagation and tissue culture of Eucalyptus. Tree Physiology 9, 435-477.*
Auderset et al. Stimulation of Root Formation by Thiol Compounds HortScience 31(2):240-242 1996.*
Norby et al. Effects of Atmospheric Co2 Enrichment on the Growth and Mineral Nutrition of *Quercus alba* Seedlings in Nutrient-Poor Soil. Plant Physiol.(1986) 82, 83-89.*
Tyburski et al. Glutathione and glutathione disulfide effect adventitious root formation and growth in tomato seedling cuttings. Acta Physiol. Plant (2010) 32:411-417. Published on line Nov. 24, 2009.*
Asada, T., "Tree Propagation Technology and Research Topics on Afforestation at Corporate Level," Forestry Research Institute, Oji Paper Company Limited (Research note, Regulation of Plant Growth & Development vol. 41, No. 1, pp. 83-89 (2006), The Japanese Society for Chemical Regulation of Plants).
Office Action mailed Jul. 2, 2013, JP Patent Application No. 2011-545244 (JP National Phase Entry of PCT/JP2010/072137) (English translation attached).
English translation of International Search Report mailed Mar. 15, 2011, International Patent Application No. PCT/JP2010/072137.
Sotelo, M., et al., "Micropropagation of *Eucalyptus maidenii* elite trees," Agrociencia (2007) vol. XI No. 1, pp. 81-89.
Belmonte, M.F., et al., "Alterations of the glutathione redox state improve apical meristem structure and somatic embryo quality in white spruce (*Picea glauca*)," Journal of Experimental Botany, vol. 56, No. 419, pp. 2355-2365, Sep. 2005, Advance Access Publication Jul. 4, 2005.
Belmonte, M.F., et al., "Glutathione-induced growth of embryogenic tissue of white spruce correlates with change sin pyrimidine nucleotide metabolism," Plant Science (2005), vol. 168, pub. 12, Nov. 12, 2004, pp. 803-812.
Imin, N., et al., "Factors involved in root formation in *Medicago truncatula*," Journal of Experimental Botany (2007), vol. 58(3), Advance Access pub. Dec. 6, 2006, pp. 439-451.

* cited by examiner

*Primary Examiner* — Annette Para
(74) *Attorney, Agent, or Firm* — Casimir Jones SC

(57) ABSTRACT

A shoot of a plant is cultivated under the presence of glutathione, so that the shoot is rooted. It is possible to cultivate the shoot under the presence of glutathione by use of a rooting medium including glutathione or by contacting a solution including glutathione with the shoot. Oxidized glutathione is preferably used as glutathione. By promoting rooting of the shoot of the plant, a rooting rate of the shoot of the plant is improved. This improves productivity of a clone seedling.

15 Claims, No Drawings

METHOD FOR PRODUCING CLONE SEEDLINGS

CROSS-REFERENCE TO RELATED APPLICATIONS

This application is a national stage of International (PCT) Patent Application Serial No. PCT/JP2010/072137, filed Dec. 9, 2010, which claims the benefit of and priority to JP Patent Application No. 2009-280017 filed Dec. 10, 2009 and JP Patent Application No. 2009-280018 filed Dec. 10, 2009, the contents of each of which are hereby incorporated by reference for all purposes.

TECHNICAL FIELD

The present invention relates to a method for producing a clone seedling, and specifically relates to (i) a method for producing a clone seedling by rooting a shoot of a plant and (ii) a rooting medium which can be suitably used for the method.

BACKGROUND ART

A step of mass-producing plant bodies (seedlings) having a trait appropriate for a purpose and being homogeneous in quality is unavoidably required in industrially using the plant bodies for the purpose of agricultural production, afforestation, breeding, etc. A conventional cutting propagation and a tissue culture method created by recent development in biotechnology are useful as means for mass-producing plant bodies. Employing those methods makes it possible not only to merely mass-produce seedlings, but also to rapidly produce a large amount of plant bodies having the same trait, i.e., clone seedlings. In particular, in order to mass-produce an excellent line of a genetically modified tree, it is necessary to vegetatively propagate seedlings of the selected line with efficiency.

In a case of the cutting propagation, a plant body is produced by preparing a cutting of a branch or a stalk, or alternatively, a terminal bud, an axillary bud, a leaf, a seed leaf, a hypocotyl, or the like in some cases, from an individual plant to be propagated, and then planting and rooting the cutting to a cutting bed or a medium. Meanwhile, in a case of mass-producing plants by use of the tissue culture method, an appropriate tissue cut from an individual plant to be propagated is cultured. Then, an adventitious bud, an adventitious embryo, a shoot primordium, or a foliage (shoot) grown from a tissue of any of them is collected and is rooted. That is, rooting is necessary no matter which method is selected to produce clone seedlings.

Accordingly, rooting ability of a plant tissue affects productivity of a clone seedling. In particular, if a plant species is low in rooting ability, the low rooting ability becomes a serious hindrance against industrial application of clone seedlings of the plant species.

It is known that various substances influence rooting of a plant tissue. One example of such a substance whose influence on rooting has been studied is ethylene that a plant tissue itself emits. In order to reduce generation of ethylene, it has been proposed to culture a tissue of an adventitious bud or the like with a medium in which silver nitrate is added (see Patent Literature 1). This method can reduce a mortality rate of the plant tissue to some extent, however, rooting of the plant tissue is suppressed or delayed. Therefore, this method would be effective to merely slightly improve the plant tissue in rooting rate, or this method would even inhibit the rooting rate of the plant tissue.

Furthermore, Patent Literature 2 discloses that (I) a rooting rate of eucalyptus is particularly improved by using a medium containing (i) silver thiosulfate ($AgS_4O_6$, Silver Thiosulfate Complex; hereinafter, abbreviated simply as "STS") serving as a source of silver ions and (ii) an ascorbic acid serving as an antioxidant, and (II) red light is more preferably used as a light source than white light. However, rooting rates of some plant species and some particular eucalyptus lines with useful trait cannot be improved sufficiently by these improvements, thereby resulting in low rooting rates that lead to low productive efficiency of seedlings. This has been a big problem for this technique.

Meanwhile, there is a report that glutathione influences differentiation of an adventitious embryo from a callus. For example, Patent Literature 3 discloses that culturing of calluses of a rice plant and a Russell prairie gentian in a medium containing glutathione promotes redifferentiation.

However, Patent Literature 4 discloses that addition of glutathione of 1 mM rather inhibits a callus of a tobacco plant from forming an adventitious bud, and addition of buthionine sulfoximine (BSO) which serves as a glutathione synthesis inhibitor remarkably increases the number of differentiation of adventitious buds per callus. This indicates that the influence of glutathione on redifferentiation of callus of a plant body differs depending on the kind of the plant body.

As described above, there has been no technique for obtaining practically enough quantity of clone seedlings from shoots; and for glutathione, it has been merely reported that glutathione influences formation of adventitious embryos of calluses of limited kinds of plant species. Under such circumstances, there has been desired an industrially useful technique for obtaining clone seedlings by efficiently rooting shoots.

CITATION LIST

Patent Literature 1

Japanese Patent Application Publication, Tokukai, No. 2001-346464 A (Publication date: Dec. 18, 2001)

Patent Literature 2

Japanese Patent Application Publication, Tokukai, No. 2006-141252 A (Publication date: Jun. 8, 2006)

Patent Literature 3

Japanese Patent Application Publication, Tokukai, No. 2004-352679 A (Publication date: Dec. 16, 2004)

Patent Literature 4

Japanese Patent Application Publication, Tokukai, No. 2008-120815 A (Publication date: May 29, 2008)

SUMMARY OF INVENTION

Technical Problem

One object of the present invention is to promote rooting of a shoot of a plant to thereby to improve a rooting rate of the shoot of the plant, thereby improving productivity of a clone seedling by use of cutting propagation, the tissue culture method, or the like, in particular, improving productivity of a clone seedling of a plant species having low rooting ability. Furthermore, another object of the present invention is to rapidly produce a large amount of clone seedlings so that the clone seedlings can be used industrially.

Solution to Problem

A method for producing a clone seedling according to the present invention includes the step of cultivating a shoot of a plant under the presence of glutathione.

In the method of the present invention, the step of cultivating may be carried out by use of a medium containing glutathione.

In the method of the present invention, a glutathione concentration in the medium is preferably within the range from 1 mg/L to 5000 mg/L, and more preferably from 1 mg/L to 100 mg/L.

In the method of the present invention, it is preferable that the medium does not contain a carbon source other than glutathione and contains nitrogen, phosphorus, and potassium as essential elements.

In the method of the present invention, the step of cultivating may be carried out by contacting a solution containing glutathione with the shoot of the plant.

In the method of the present invention, a glutathione concentration in the solution is preferably within the range from 1 mg/L to 5000 mg/L, and more preferably from 1 mg/L to 100 mg/L.

In the method of the present invention, it is preferable that glutathione is oxidized glutathione.

In the method of the present invention, the plant may be a plant which is hardly rooted. In this case, it is preferable that the plant is selected from the group consisting of eucalyptus plants, pinus plants, prunus plants, mangifera plants, and avocado plants. It is more preferable that the plant is a eucalyptus plant.

In the method of the present invention, it is preferable that the step of cultivating is carried out under irradiation of light having a wavelength component of 650 nm to 670 nm to a wavelength component of 450 nm to 470 nm at a ratio of 9:1 to 7:3.

In the method of the present invention, it is preferable that the step of cultivating is carried out under carbon dioxide gas supply.

In the method of the present invention, it is preferable that a supplying amount of the carbon dioxide gas is in a range from 300 ppm to 2000 ppm.

In the method of the present invention, it is preferable that the step of cultivating is carried out under a humidity of 80% or more.

The method of the present invention may be carried out by use of the shoot having a base wounded.

In the method of the present invention, it is preferable that the shoot is any one of (i) a cutting, (ii) a multiple shoot which is obtained by culturing an organ under a sterile condition, wherein the organ is collected from a mother plant, and (iii) a foliage which is obtained by breeding the organ under a sterile condition.

A composition of the present invention includes glutathione in order to root a shoot of a plant.

It is preferable that the composition of the present invention is for use as a medium.

In the composition of the present invention, it is preferable that a glutathione concentration in an amount is within the range from 1 mg/L to 5000 mg/L, and more preferably from 1 mg/L to 100 mg/L.

The composition of the present invention may be used as an auxiliary agent which is to be added in a medium or a solution. It is preferable that the composition gives a final concentration of glutathione within the range from 1 mg/L to 5000 mg/L to the medium or solution to which the composition is added, and it is more preferable that the composition gives a final concentration of glutathione within the range from 1 mg/L to 100 mg/L to the medium or solution to which the composition is added. Further, it is preferable that the composition is in the form of tablet, powder or granule.

It is preferable that the composition of the present invention is for carrying out asexual reproduction of the plant. The composition also may be used for preparing a clone seedling from the shoot of the plant.

In the composition of the present invention, it is preferable that the glutathione is oxidized glutathione.

In the composition of the present invention, it is preferable that the composition does not comprise a carbon source other than glutathione. It is preferable that the composition comprises nitrogen, phosphorous and potassium as essential elements.

In the present invention, glutathione is used to root the shoot of the plant. It is more preferable to use glutathione for preparing the clone seedling from the shoot of the plant. Furthermore, in the present invention, glutathione is used to prepare a composition for rooting the shoot of the plant. It is more preferable to use glutathione in order to prepare the composition for preparing the clone seedling from the shoot of the plant.

Advantageous Effects of Invention

According to the present invention, a shoot of a plant is cultivated under the presence of glutathione, so that rooting of the shoot is promoted and therefore a rooting rate is improved. This improves productivity of clone seedlings. In addition, such effect is remarkable in particular with respect to a plant species having low rooting ability. Accordingly, the present invention contributes to quick mass-production of widely various plant species of clone seedlings. In particular, even for a plant species having low rooting ability, the present invention can quickly mass-produce a clone seedling of such a plant species so that the plant species having low rooting ability becomes industrially applicable.

DESCRIPTION OF EMBODIMENTS

[Method for Propagating Plant]

Plants are bred by seed propagation (sexual reproduction) or vegetative propagation (asexual reproduction). In breeding plants, there is a demand for producing a large number of individuals each having an excellent trait. Such individuals are obtained in such a manner that (i) excellent individuals suitable for a predetermined purpose are selected from a large number of individuals which are different from each other genetically, and (ii) the excellent individuals thus selected are clonally propagated by use of vegetative propagation. Clone seedlings are thus obtained. The vegetative propagation is a technique for increasing individuals of the same trait, and examples of the vegetative propagation encompass cutting, grafting, layering, and division.

The cutting is a technique for forming an independent individual by (i) collecting a part of a plant of interest and (ii) producing an adventitious root or an adventitious bud therefrom on a cutting bed. The cutting is an easy technique which can be the most widely used. However, it is extremely difficult to apply the technique to a plant having low rooting ability. The grafting is a technique for attaching a part of a plant of interest to another plant to grow the plant of interest and the another plant as one individual. The grafting therefore can breed the plant of interest even if the plant of interest cannot be bred by cutting and layering. However, it is extremely technically difficult to realize the breeding by use of grafting. The layering is used when a plant cannot be bred by grafting and cutting, however, has poor reproductive efficiency.

In order to try cutting, various rooting promoter (e.g., auxin) are often used because rooting ability of a plant of interest is important. It is also known that a concentration of agar, sucrose, etc. in a rooting medium affect form of a root grown therein. Further, activated carbon exhibits root promoting effect for some plants, such as Japanese cypress. Furthermore, it is also known that rooting of some shoots is promoted when the shoots are planted in a non-sterile state.

As described above, there is a demand for stably supplying seedlings by use of vegetative propagation. For that purpose, it is desired to develop an efficient method for producing clone seedlings.

The present invention relates to production of a clone seedling from a shoot of a plant. Specifically, the present invention is a technique for cultivating a shoot of a plant in the presence of glutathione to root the shoot. The present invention can promote rooting of shoots of the plant, thereby improving their rooting rate so that clone seedlings can be produced. That is, the present invention is an extremely efficient technique which can improve productivity of clone seedlings.

[Applicable Plant]

The present invention is applicable to any plants. Among them, the present invention is preferably applied to arboreous plants, and is more preferably applied to arboreous plants which are inferior to herbaceous plants in rooting ability because the present invention can be more remarkably effective to make contribution. Examples of arboreous plants encompass eucalyptus plants, pinus plants, prunus plants (prunus spp., prunus mume, prunus tomentosa, etc.), avocado plants, mangifera plants (mangifera indica etc.), acacia plants, myrica plants, quercus plants (quercus acutissima etc.), vitis plants, malus plants, rosa plants, camellia plants, jacaranda plant (jacaranda mimosifolia etc.), and persea plants (persea americana etc.). Among them, the present invention can make more effective when the present invention is applied to eucalyptus, pinus, prunus, mangifera, avocado, acacia, myrica, quercus, vitis, malus, rosa, camellia, prunus mume, prunus tomentosa, jacaranda, etc. Among them, eucalyptus plants, pinus plants, prunus plants, and mangifera plants are preferable. In particular, the present invention can be more preferably applied to eucalyptus, pinus, prunus, mangifera, avocado, etc. known as plants which are hardly rooted.

Among eucalyptuses, eucalyptus plants such as *Eucalyptus globulus* and *Eucalyptus smithii* are plants having a particularly low rooting ability. The present invention can be more preferably applied to those eucalyptus plants. Note that the eucalyptuses have extremely low rooting ability, and it is known that the *Eucalyptus globulus* elite tree has a rooting rate of about 25% at the most even in the presence of auxin (see, for example, Sotelo, M. and Monza, J. Agrociencia (2007) Vol XI, No. 1, p. 81-89).

[Shoot]

The wording "shoot" herein means any kinds of tissues having rooting ability. Examples of the tissues encompass a branch, a stem, a terminal bud, an axillary bud, an adventitious bud, a leaf, a seed leaf, a hypocotyl, an adventitious embryo, and a shoot primordium. Derivation of the shoot is not particularly limited, and the shoot may be (i) one obtained from an individual plant which is cultivated in a greenhouse or outdoors, (ii) a cultured tissue obtained by the tissue culture method, or (iii) a part of a wild plant body. The wording "clone seedlings" means seedlings obtained by rooting those tissues. Further, a shoot can be efficiently obtained from a mother plant of a cutting or a multiple shoot. Among them, the cutting (which has been obtained from its mother plant), the a multiple shoot obtained by cultivating, under a sterile condition, an organ which has been collected from the mother plant, or a foliage obtained by breeding the organ under a sterile condition is preferable.

A multiple shoot can be induced by culturing a tissue obtained by (i) cutting a terminal bud, an axillary bud, etc. off from a plant whose clone seedling will be produced by applying the present invention. Preparation of a multiple shoot by culturing, under a sterile condition, an organ which has been collected from a mother plant can be carried out by adopting a method and conditions described in Japanese Patent Application Publication, Tokukaihei, No. 8-228621 A, for example, for obtaining the multiple shoot from the arboreous plant. The method and the condition are substantially as follows. First, tissues such as a terminal bud and an axillary bud are collected from a material plant, and these tissues thus collected are subjected to surface disinfection by dipping, for about 10 minutes to 20 minutes, the tissues in (i) an aqueous sodium hypochlorite solution containing an available chlorine amount of about 0.5% to about 4% or (ii) an aqueous hydrogen peroxide containing an available chlorine amount of about 5% to about 15%. Then, these tissues are washed with sterilized water and planted to a solid medium. After a bud is opened, then a foliage thus grown is subcultured in a medium identical with the solid medium in composition. The subculturing produces a multiple shoot. In a case where tissues (e.g., axillary buds) of eucalyptus and acacia are used, it is preferable to use, as a solid medium, (I) a Murashige and Skoog (hereinafter, referred to as "MS") medium which contains (i) sucrose of 1 wt % to 5 wt %, (ii) benzyladenine (hereinafter, referred to as "BA") serving as a plant hormone of about 0.02 mg/L to about 1 mg/L, and (iii) gellan gum of about 0.2 wt % to about 0.3 wt % or agar of about 0.5 wt % to about 1 wt %, or (II) a modified MS medium in which ammonium nitrate component and potassium nitrate component of the MS medium are reduced by half. From the multiple shoot thus formed, shoots vigorously grows. It is possible to keep the multiple shoot by dividing the multiple shoot into some parts appropriately and culturing one of the parts of the multiple shoot in a medium having the same composition as that of the medium in which the multiple shoot is grown.

[Cutting]

As described above in the present invention, it is possible to use a cutting as a shoot when cultivating a shoot of a plant. Examples of the cutting encompass a softwood (current year's branch) and a hardwood (a branch which has been growing since previous year or before), and in addition, a bud and a leaf. In a case of an arboreous plant, a softwood or a hardwood is usually used as a cutting, meanwhile, in a case of a herbaceous plant, a leaf or a bud is usually used as a cutting.

[Glutathione]

In the present invention, glutathione is used for cultivating the shoot. A manufacturing condition of glutathione is not particularly limited, so that glutathione can be artificially synthesized or can be derived from a natural product. Further, a purity of glutathione does not matter particularly. Commercially available glutathione can be used. There are two kinds of glutathione, i.e., oxidized glutathione and reduced glutathione. Both glutathione can be used in the present invention, however, oxidized glutathione is preferable. It is deduced that, in a case where oxidized glutathione is used as glutathione in the present invention, oxidized glutathione is taken in a plant body, and then, in the plant body, the oxidized glutathione is changed to reduced glutathione having more excellent stability.

A step of cultivating a shoot of a plant in the presence of glutathione can be appropriately selected on the basis of the kinds of plant, a state of the shoot, a cultivating method, and/or the like. Examples of the step of cultivating encompass a method for culturing the shoot in a rooting medium containing glutathione and a method for contacting a solution containing glutathione with the shoot. In a case where a cultured tissue which has been obtained by the tissue culture method is used as a shoot, the former method is preferable. In a case where a cutting is used as a shoot, any of the former and the latter methods can be used. Note that, as a matter of course, a combined method of the exemplified methods (that is, a method in which the shoot is contacted with a solution containing glutathione while the shoot is cultured in a rooting medium containing glutathione) can be employed in the present invention.

In a case where the shoot is cultured in the rooting medium containing glutathione, a glutathione concentration in the rooting medium is preferably within the range from about 1 mg/L to about 5000 mg/L, more preferably from about 5 mg/L to about 1000 mg/L, and most preferably about 25 mg/L to about 500 mg/L.

In a case where (i) the shoot is cultured in the rooting medium and (ii) a supporter to which few active substances stick (such as oasis) is used as described below, an amount of glutathione to be added to the rooting medium preferably is within the range from about 1 mg/L to about 100 mg/L, more preferably from about 5 mg/L to about 75 mg/L, and most preferably about 25 mg/L to about 75 mg/L.

In a case where the solution containing glutathione (glutathione solution) is brought into contact with the shoot, a method for contacting the shoot with glutathione is not particularly limited, and can be appropriately selected on the basis of the kinds of plant, a state of the shoot, a culture method, or the like. Examples of the method encompass a method for directly spraying the glutathione solution to the shoot and a method for causing the supporter to infiltrate with the glutathione solution.

The glutathione solution can be prepared by dissolving glutathione into an appropriate solvent (e.g., water etc.). Examples of water encompass deionized water, distilled water, reverse osmosis water, and tap water. Any water can be used. The glutathione concentration in the glutathione solution preferably is within the range from about 1 mg/L to about 5000 mg/L, more preferably from about 5 mg/L to about 1000 mg/L, and most preferably about 10 mg/L to about 1000 mg/L.

In a case where the glutathione solution is directly sprayed to the shoot, the glutathione solution may be sprayed to a part of or a whole shoot in the form of a mist by use of a spray etc. A spray amount of the glutathione solution changes depending on the glutathione concentration in the glutathione solution, and hence, cannot be specifically defined. However, generally, the spray amount preferably is within the range from about 0.5 ml to about 5.0 ml and more preferably from about 1.0 ml to about 3.0 ml per shoot. The number of spraying may be one, two, or more, and it is preferable that the glutathione solution is sprayed at least when cultivation of the shoot is started. Furthermore, the glutathione solution can be additionally and appropriately (e.g., every few (two to three) days) sprayed in accordance with a cultivation condition during a cultivation period.

Examples of the method for infiltrating the supporter with the glutathione solution encompass: a method for spraying the glutathione solution from above the supporter; and a method for placing the supporter in a container filled with the glutathione solution so as to infiltrate the supporter from its bottom. In a case of spraying the glutathione solution from above of the supporter, an amount of spraying water from the above preferably is within the range from about 1.0 ml to about 30 ml, and more preferably from about 5.0 ml to about 10.0 ml per shoot. In a case of infiltrating the supporter from the bottom, the supporter may be substantially and uniformly infiltrated with the glutathione solution. In a case where the supporter is infiltrated with the glutathione solution, another rooting medium is prepared in addition to the glutathione solution, the supporter may be infiltrated from both the above and the bottom, as described above already.

In a case where the glutathione-containing medium (rooting medium) or the glutathione solution is prepared, glutathione may be provided as an auxiliary agent which is added to and mixed with the medium or the solution. In order to successfully prepare the rooting medium or the glutathione solution, glutathione is preferably in form of tablet, powder, or granule. Glutathione is contained in the auxiliary agent so that a final concentration of glutathione in the rooting medium or the glutathione solution thus prepared is within the aforementioned range.

It is preferable that the glutathione-containing medium or the glutathione solution is supplied to a plant after the glutathione concentration is adjusted to is within the aforementioned concentration range. However, it is only necessary to mix glutathione with the medium or the solution when glutathione is taken in the plant. It is therefore possible to simultaneously or continuously supply, directly to an outer surface of the plant or a vicinity (the supporter or soil) of the plant, (i) a medium or a solution which does not contain glutathione and (ii) an auxiliary agent. In this way, the plant can take in the medium or the solution with which an auxiliary agent is mixed.

[Rooting Medium]

The wording "rooting medium" in the present invention means a medium for rooting a shoot of a plant. The rooting medium preferably contains silver ions and/or an antioxidant, and more preferably contains both the silver ions and the antioxidant. The silver ions can be added to the medium as STS or a silver compound (silver ion source) such as silver nitrate. Especially, in a case where the shoot is cultured in the medium added with STS, healthy rooting and root growth can be promoted. Accordingly, STS is preferably used as the silver ion source for use in the present invention. The reason why STS can promote the healthy rooting and root growth is presumably that the silver ions derived from STS are in the form of silver thiosulfate ions in the medium, and the silver thiosulfate ions are negatively charged. A silver ion concentration added to the rooting medium changes depending on the kind of silver ion source, other culture conditions, etc., however, the silver ion concentration is preferably within the range from about 0.5 µM to about 10 µM, and more preferably from about 2 µM to about 6 µM.

Meanwhile, examples of the antioxidant encompass well-known antioxidants such as an ascorbic acid and sulfite. Among them, an ascorbic acid has low persistence with respect to the medium, so that the ascorbic acid is preferably used as an antioxidant for use in the present invention. A concentration of antioxidant added to the rooting medium is preferably within the range from about 5 mg/L to about 200 mg/L, and more preferably from about 20 mg/L to about 100 mg/L.

The rooting medium for use in the present invention can include, in addition to the aforementioned components, inorganic components, carbon sources, vitamins, amino acids, plant hormones, etc.

Examples of the inorganic components encompass: chemical elements such as nitrogen, phosphorous, potassium, sulfur, calcium, magnesium, iron, manganese, zinc, boron, molybdenum, chlorine, iodine, and cobalt; and an inorganic salt containing at least one kind of chemical element. Examples of the inorganic salt encompass potassium nitrate, ammonium nitrate, ammonium chloride, sodium nitrate, dipotassium phosphate, sodium dihydrogenphosphate, potassium chloride, magnesium sulfate, ferrous sulfate, ferric sulfate, manganese sulfate, zinc sulfate, copper sulfate, sodium sulfate, calcium chloride, magnesium chloride, boric acid, molybdenum trioxide, sodium molybdate, potassium iodide, cobalt chloride, etc., and hydrates of them. One kind of inorganic component selected from the above specific examples can be used alone, or two or more kinds of inorganic components can be used in combination. The rooting medium for use in the present invention preferably contains nitrogen, phosphorous, and potassium as essential elements. Accordingly, among the specific examples of the inorganic components, nitrogen, phosphorous, potassium, inorganic salt containing nitrogen, inorganic salt containing phosphorous, and inorganic salt containing potassium are preferable, and nitrogen, phosphorous, potassium, and inorganic salt containing nitrogen are more preferable. In a case where one kind of the inorganic components is used, it is preferable that the inorganic component is added to the rooting medium so that the concentration in the rooting medium is preferably within the range from about 1 µM to about 100 mM, and more preferably from about 0.1 µM to about 100 mM. In a case where two or more kinds of the inorganic components are used, it is preferable that each of the inorganic components is added to the rooting medium so that the concentration in the rooting medium preferably is within the range from about 0.1 µM to about 100 mM, and more preferably from about 1 µM to about 100 mM.

The following compounds can be used as a carbon source: carbohydrate such as sucrose and derivatives thereof; organic acid such as fatty acid; and primary alcohol such as ethanol. One kind of the carbon sources selected from the specific examples can be used alone, or two or more kinds of the carbon sources can be used in combination. It is preferable that the carbon source(s) is(are) added to the rooting medium so as to is within the range from about 1 g/l to about 100 g/l, and more preferably from about 10 g/l to about 100 g/l. However, in a case of culturing a shoot under carbon dioxide gas supply, the medium does not need to include a carbon source, and it is preferable that the medium does not include a carbon source. An organic compound which can be a carbon source of sucrose etc. could also serve as a carbon source of microbes. Accordingly, in a case of using a medium added with the carbon dioxide gas or the organic compound, it is necessary to culture the shoot under an aseptic environment. However, it is possible to culture the shoot under a non-aseptic environment when using a medium which does not include any carbon sources other than glutathione.

The examples of vitamins encompass biotin, thiamin (vitamin B1), pyridoxine (vitamin B4), pyridoxal, pyridoxamine, calcium pantothenate, inositol, nicotinic acid, nicotinamide, and/or riboflavin (vitamin B2). One kind of the vitamins selected from the above specific examples can be used alone, or two or more kinds of the vitamins can be used in combination. In a case where one kind of the vitamins is used, it is preferable that the vitamin is added to the rooting medium so that a concentration in the rooting medium is within the range from about 0.01 mg/L to about 200 mg/L, and more preferably from about 0.02 mg/L to about 100 mg/L. In a case where two or more kinds of the vitamins are used, it is preferable that each of the vitamins is added to the rooting medium so as to is within the range from about 0.01 mg/L to about 150 mg/L, and more preferably from about 0.02 mg/L to about 100 mg/L.

The examples of amino acids encompass glycine, alanine, glutamic acid, cysteine, phenylalanine, and/or lysine. One kind of the amino acids selected from the specific examples can be used alone, or two or more kinds of the amino acids can be used in combination. In a case where one kind of the amino acids is used, it is preferable that the amino acid is added to the rooting medium so that a concentration in the rooting medium is within the range from about 0.1 mg/L to about 1000 mg/L. In a case where two or more kinds of the amino acids are used, it is preferable that each of the amino acids is added to the rooting medium so as to is within the range from about 0.2 mg/L to about 1000 mg/L.

Further, plant hormones such as auxins and/or cytokinins can be used. Examples of auxins encompass naphthaleneacetic acid (NAA), indoleacetic acid (IAA), p-chlorophenoxyacetic acid, 2,4-dichloropfenoxyacetic acid (2,4-D), indolebutyric acid (IBA), and derivatives thereof. One kind or two or more kinds of the auxins, selected from those examples, can be used alone or in combination. Further, examples of cytokinins encompass benzyladenine (BA), kinetin, zeatin, and derivatives thereof. One kind or two or more kinds of cytokinins, selected from those examples, can be used alone or in combination. As a plant hormone, only auxins or only cytokinins can be used, or both auxins and cytokinins can be used in combination. In a case where one kind of the plant hormones is used, it is preferable that the plant hormone is added to the rooting medium so that a concentration in the rooting medium is within the range from about 0.01 mg/L to about 10 mg/L, and more preferably from about 0.02 mg/L to about 10 mg/L. In a case where two or more kinds of the plant hormones are used, it is preferable that each of the plant hormones is added to the rooting medium so as to is within the range from about 0.01 mg/L to about 10 mg/L, and more preferably from about 0.02 mg/L to about 10 mg/L.

Note that, in the present invention, a medium well-known as a medium for cultivating a plant tissue which is added with glutathione as necessary, and is also added with silver ions and/or an antioxidant, a carbon source other than glutathione, and a plant hormone can be used as a rooting medium. Examples of the medium for cultivating a plant tissue encompass an MS medium, a phosphorous Linsmaier 86 Skoog medium, a White's medium, a Gamborg's B5 medium, and a Nitsch and Nitsch medium. Among them, the MS medium and the Gamborg's B5 medium are preferable. It is possible to use those mediums by appropriately diluting the mediums as necessary.

A liquid medium and a solid medium can be used as the rooting medium, however, a liquid medium is preferable in (i) work efficiency and (ii) low possibility of wounding the shoot during transplant of the shoot. In a case where the liquid medium is used, it is possible to use the liquid medium only by mixing compositions of the medium. Meanwhile, in a case where the solid medium is used, compositions of the medium are added in the same way as the liquid medium, and simultaneously with or after the mixing, the mixture is fixed by a gelling agent such as agar or gellan gum. The gelling agent to be added to the medium changes depending on the kind of the gelling agent and the composition of the medium. In a case where the gelling agent is agar, the amount is preferably 0.5 wt % to 1 wt %. In a case where the gelling agent is gellan gum, the amount is preferably 0.2 wt % to 0.3 wt %.

A method for planting a shoot to a rooting medium can be appropriately selected on the basis of the kind of medium, a culture condition, etc. In a case where the rooting medium is a solid medium, a base of the shoot may be directly planted to the rooting medium to thereby be cultured. Meanwhile, in a case where the rooting medium is a liquid medium, the base of the shoot may be planted to, for example, a member in which a supporter (described below) is infiltrated with the rooting medium. Note that, when the shoot is planted to the rooting medium, providing physical stimulation (e.g. wounding the base of the shoot) is preferable for improving a rooting ratio. The base of the shoot means a part of the shoot (one end of the shoot) in which roots are formed (a part opposite to an end part in which leaves are formed). In a case where a multiple shoot is used as a shoot, the base is a part including a cross-section obtained when the multiple shoot is divided. A size (dimension, shape, etc.) of a wound to the base of the shoot is not particularly limited. For example, in a case where a multiple shoot is used as a shoot, it is preferable to wound the base of the shoot (the aforementioned cross-section) so as to have a cross-shaped wound seen from a front direction. When wounding the base of the shoot, it is possible to use a pair of scissors, a knife, or the like.

As described above, it is possible to use glutathione for the purpose of rooting a shoot of a plant. Further, it is possible to use glutathione for the purpose of asexually reproducing a plant.

In order to realize such purposes, glutathione serving as a compound can be directly used, a composition containing glutathione can be used, or a glutathione or a composition provided in a kit can be used. As described above, examples of the composition of the present invention encompass a rooting medium (glutathione-containing medium), a solution containing glutathione (glutathione solution or a glutathione-containing solution), and an auxiliary agent. However, the compositions are not limited thereto. The wording "composition" generally means "two or more kinds of components exist uniformly as a whole, and the components are considered as one substance". The "composition" used in the Specification indicates a state in which various components are contained in one material. Further, the wording "kit" used in the Specification indicates a kit in which various components to be contained in the composition are contained in respective containers (e.g., bottle, plate, tube, and dish), and all of the containers are packed together. The "kit" may include the supporter (described below) or a culture container.

[Supporter]

A supporter in the present invention is a supporter for supporting a shoot of a plant. In a case of using a rooting medium (in particular, a solid medium), a supporter is sometimes unnecessary, but is usually used.

A supporter capable of supporting the shoot which is planted during a cultivation period is preferable. Further, in the present invention, in a case where a liquid rooting medium is used for cultivating the shoot, the supporter is normally used while being infiltrated with the liquid rooting medium. Accordingly, supporters which are infiltrated with liquid are preferable. Among them, it is preferable to use a supporter which is substantially and uniformly infiltrated with a glutathione solution or a liquid medium containing glutathione. In a case where a liquid medium is used as a rooting medium, a liquid medium (which does not contain a glutathione solution) and a glutathione solution may be separately added to a supporter, or alternatively, a liquid medium containing glutathione thus prepared in advance may be added to a supporter. A conventionally used supporter can be used as a supporter, and the supporter is not particularly limited. Examples of the supporter encompass natural soil such as sand and akadama soil; artificial soil such as carbonized chaff, coconut fiber, vermiculite, perlite, peat moss, and glass beads; and porous molded product such as foaming phenolic resin and rock wool. The supporter is put into a culture container, and is infiltrated with the glutathione solution or the liquid medium containing glutathione. In this way, a rooting bed can be prepared. Note that, in a case where the rooting medium is a solid medium, a rooting bed can be prepared by putting the solid medium as it is in a culture container.

[Culture Container]

In the present invention, it is possible to use a culture container in order to store a rooting medium or a supporter. A conventionally used culture container can be used as a culture container, and the culture container is not particularly limited. Examples of the culture container encompass a seedling pot and a plug tray. A sealed culture container and an open culture container can be used, however, a sealed culture container is preferable. By using a sealed culture container, it is possible to keep sprayed glutathione in the sealed culture container. Further, the sealed culture container easily keeps a humidity of an environment surrounding a shoot or a clone seedling to be formed.

In a case where a branch is used as a shoot, it is preferable to use a sealed culture container as a culture container. Accordingly, the shoot can be easily placed under a high humidity. This means transpiration of leaves on a branch is suppressed. It is therefore possible to omit a process for partially cutting leaves, which process is conventionally performed.

It is more preferable that a culture container is a container which can supply carbon dioxide gas into a container. Examples of such culture container encompass a container having an opening which is covered with a carbon dioxide permeable membrane. By using the container, it is possible to easily adjust a humidity of a culture environment. A shape of the opening does not matter particularly. A material of carbon dioxide permeable membrane is not particularly limited, and, for example, polytetra-fluoroethylene can be used. Further, a pore size of the film is not particularly limited, and for example, a film having a pore size of about 0.1 µm to about 1 µm is used.

[Cultivation Condition]

A cultivation condition for cultivating a shoot is not particularly limited, provided that the shoot can root. It is difficult to specifically define the cultivation condition because the cultivation condition would change depending on the kind of plant, a state of a shoot, the kind of rooting medium, etc. However, it is more preferable that, for example, the cultivation is carried out at a temperature within the range from about 23° C. to about 28° C. Light intensity is indicated as a photosynthesis photon flux density, and it is preferable that the photosynthesis photon flux density is within the range from about 10 µmol/m$^2$/s to about 1000 µmol/m$^2$/s, and more preferably from about 50 µmol/m$^2$/s to about 500 µmol/m$^2$/s. In any case, rooting of a shoot can be observed usually within about two weeks to about five weeks.

It is preferable to cultivate the shoot under irradiation of light which has a wavelength component of 650 nm to 670 nm to a wavelength component of 450 nm 470 nm at a ratio of 9:1 to 7:3, and more preferably, 9:1 to 8:2. By cultivating the shoot under the irradiation of the light including those wavelength components, rooting of the shoot can be more promoted.

Furthermore, it is preferable to supply carbon dioxide gas of normally 300 ppm to 2000 ppm into a cultivation environment, and it is more preferable to supply carbon dioxide gas of 800 ppm to 1500 ppm thereinto. A supply amount of carbon dioxide gas can be controlled by use of, for example, equipment such as an incubator or a culture container having an opening which is covered with a carbon dioxide permeable membrane.

The humidity is preferably 80% or more, and more preferably 85% or more. This humidity makes it possible to promote rooting of the shoot. Note that an upper limit of the humidity is not particularly limited.

It is preferable to shield light when a cutting is used as a shoot. A light shielding rate is preferably in a range from 30% to 70%, and more preferably from 40% to 60%.

As described above, a clone seedling rooted from the shoot can be obtained. A shoot thus obtained is continued to be cultured as necessary for a certain period of time. After the shoot roots to have a root grown enough, the shoot is transplanted to a seedling container, a nursery, or the like, and is bred. In this way, a seedling which is usable for a predetermine purpose, such as afforestation, can be bred. Soil to be used and conditions, such as a temperature and light intensity, during the breeding of the shoot may be appropriately selected for the plant. Note that, in a case where the rooted shoot is a shoot derived from a cultured tissue, such as an adventitious bud or a shoot primordium, it is normally necessary to carry out an acclimation step before the shoot is transplanted to a seedling container etc.

[Effect]

In the present invention, it is possible to root a shoot of a plant by cultivating the shoot in the presence of glutathione. The reason of this is considered as follows.

Glutathione is generally known as an antioxidant, and it is considered that glutathione can reduce active oxygen stress in cells. However, there is no knowledge to clearly prove that an oxidation-reduction reaction relates to rooting of a plant. Meanwhile, carbon dioxide fertilization and light have an effect on rooting of a plant. From this, there is a high possibility that potentiation of photosynthesis relates to a root promoting effect of glutathione in some way.

EXAMPLES

Hereinafter, the present invention will be described in detail below by Examples.

Example 1

A foliage (shoot) grown to have a length of 2 cm to 5 cm was cut from a multiple shoot induced from a wild-type *Eucalyptus globulus* (hereinafter, abbreviated simply as an "*E. globulus*"). Inducing the multiple shoot followed a method described in Japanese Patent Application Publication, Tokukaihei, No. 8-228621 A. Specifically, a tissue (terminal bud and axillary bud) was collected from *E. globulus* (wild type), and the tissue thus collected was subjected to surface disinfection by immersing the tissue for twenty minutes in an sodium hypochlorite aqueous solution containing an amount of available chlorine of 1%. Then, the tissue which had been subjected to the surface disinfection was washed by sterilized water and was planted to a solid medium (MS medium containing sucrose of 20 gwt %, BA of 0.2 mg/L, and gellan gum of 2.5 gwt %), and its bud was opened. Within three and four weeks after the culturing of the foliage was started, the culturing of the foliage was subcultured in a medium having a composition identical with that described above. A multiple shoot was formed as a result of the subculturing. Note that the foliages from the multiple shoot was grown in a medium having the composition identical with that used for forming the multiple shoot under the condition identical with that used for forming the multiple shoot.

A base of the shoot thus obtained was planted to a foaming phenolic resin porous supporter (Manufactured by Smithers-Oasis Company; Product name: Oasis). The supporter had been infiltrated with a 4-fold diluted MS medium (Composition: ammonium nitrate of 412.5 mg/L, potassium nitrate of 475 mg/L, potassium dihydrogenphosphate of 42.52 mg/L, potassium iodide of 0.21 mg/L; Note that any carbon source other than glutathione is not added to this medium.) to which oxidized glutathione of 25 mg/L, STS ($AgS_4O_6$) serving as a silver ion source of 5 μM, an ascorbic acid serving as an antioxidant of 50 mg/L, and IBA serving as a plant hormones of 2 mg/L were added. The base of the shoot was cultured for two months in carbon dioxide gas of 1000 ppm at a temperature of 25° C. under irradiation of red light having photosynthesis photon flux density of 51.3 μmol/m²/S and having a wavelength component of 650 nm to 670 nm to a wavelength component of 450 nm to 470 nm at a ratio of 8.2:1.8. The culturing was carried out with a culture container, which was a cube container (maximum size of about 10 cm to 11.5 cm in length×10 cm to 11.5 cm in width×10.0 cm in height) having a shape whose bulge was slightly protruded. A top surface of the culture container had a circular opening which was covered with a polytetra-fluoroethylene film (Manufactured by Millipore Corporation, Product name: Milli-Seal) having a pore size of 0.45 μm. Carbon dioxide gas outside the culture container was allowed to enter the culture container through this carbon dioxide gas permeable membrane covering the opening. Accordingly, carbon dioxide gas concentration inside the culture container was about 1000 ppm due to the permeation of the carbon dioxide gas through the film covering the opening of the culture container. The culture container was irradiated with red light by use of a light irradiation device (Product name: CCFL unit, maker's name: Nippon Medical & Chemical Instruments CO., LTD.). Further, humidity in the culture container is adjusted by sealing the culture container with Parafilm.

Nine shoots were planted per culture container. A rooting rate was calculated from the number of test pieces of the shoot and the number of shoots (the number of rooted shoots) which had been rooted after the foliage was cultured for two months. The result is shown in Table 1.

Example 2

The culture was carried out in the same way as Example 1, except that an amount of oxidized glutathione to be added to the medium was 50 mg/L. The result is shown in Table 1.

Example 3

The culture was carried out in the same way as Example 1, except that the amount of oxidized glutathione to be added to the medium was 75 mg/L. The result is shown in Table 1.

Comparative Example 1

The culture was carried out in the same way as Example 1, except that oxidized glutathione was not added to the medium. The result is shown in Table 1.

TABLE 1

|  | Variety name | Oxidized glutathione concentration in medium (mg/L) | How to provide glutathione | Number of test pieces of shoot | Number of rooted shoots | Rooting rate (%) |
|---|---|---|---|---|---|---|
| Example 1 | E. globulus wild-type (tissue culture) | 25 | adding glutathione to rooting medium | 27 | 20 | 74.1 |
| Example 2 | E. globulus wild-type (tissue culture) | 50 | adding glutathione to rooting medium | 27 | 23 | 85.2 |
| Example 3 | E. globulus wild-type (tissue culture) | 75 | adding glutathione to rooting medium | 27 | 14 | 51.9 |
| Comparative Example 1 | E. globulus wild-type (tissue culture) | 0 | — | 27 | 6 | 22.2 |

As is clearly from Table 1, a rooting rate of each of Examples 1 to 3 (in which oxidized glutathione of 25 mg/L to 75 mg/L was added to a rooting medium) was high, i.e., 51.9% to 85.2%, whereas a rooting rate of Comparative Example 1 (in which oxidized glutathione was not added to a rooting medium) was low, i.e., 22.2%.

Example 4

A crossbreed of *Eucalyptus urophylla* and *Eucalyptus grandis* (hereinafter, abbreviated as an "*E. uro-grandis*") (Line name: A) was used as a material of a cutting. Specifically, a graft grown to have a length of about 5 cm to 20 cm, about one to three joints, and about two to six leaves was cut out from a mother tree, and a tip of each leaf was cut off by cutting off about a half from the tip thereof. In this way, the cutting was prepared.

A composite soil of carbonized chaff, coconut fiber, and vermiculite which had been put into a seedling pot (3 cm in inner diameter×15 cm in height) in advance was used as a supporter. Oxidized glutathione was dissolved in water so that an oxidized glutathione concentration became 50 mg/L. The oxidized glutathione solution was thus prepared. The oxidized glutathione solution was sprayed to the seedling pot from the above by use of a watering can so that the supporter was soaked with the oxidized glutathione solution (50 mg/L) by spraying a spray amount of water of about 8.5 ml of the oxidized glutathione solution per seedling pot. Thereafter, a base of the cutting was planted to the supporter. After this planting, the cutting was bred for three weeks in a green house which shielded sunlight by 50%. In the green house, a high humidity (80% or more) was kept by frequently spraying mist. After three weeks from the planting, a rooting ratio was calculated from the number of rooted cuttings. The result is shown in Table 2.

Example 5

A seedling was bred in the same way as Example 4, except that a solution having an oxidized glutathione concentration of 200 mg/L was used as the oxidized glutathione solution. The result is shown in Table 2.

Example 6

A seedling was bred in the same way as Example 4, except that a solution having an oxidized glutathione concentration of 500 mg/L was used as the oxidized glutathione solution. The result is shown in Table 2.

Example 7

A seedling was bred in the same way as Example 4, except that a solution having an oxidized glutathione concentration of 1000 mg/L was used as the oxidized glutathione solution. The result is shown in Table 2.

Comparative Example 2

A seedling was bred in the same way as Example 4, except that the oxidized glutathione solution was not sprayed. The result is shown in Table 2.

TABLE 2

|  | Variety name | Sprayed oxidized glutathione concentration (mg/L) | How to provide glutathione | Number of test pieces of shoot | Number of rooted shoots | Rooting rate (%) |
|---|---|---|---|---|---|---|
| Example 4 | E. uro-grandis A | 50 | spraying to supporter | 44 | 33 | 75.0 |
| Example 5 | E. uro-grandis A | 200 | spraying to supporter | 44 | 34 | 77.3 |

TABLE 2-continued

| | Variety name | Sprayed oxidized glutathione concentration (mg/L) | How to provide glutathione | Number of test pieces of shoot | Number of rooted shoots | Rooting rate (%) |
|---|---|---|---|---|---|---|
| Example 6 | E. uro-grandis A | 500 | spraying to supporter | 44 | 37 | 84.1 |
| Example 7 | E. uro-grandis A | 1000 | spraying to supporter | 176 | 128 | 72.7 |
| Comparative Example 2 | E. uro-grandis A | 0 | — | 44 | 25 | 56.8 |

As is clearly from Table 2, a rooting rate of each of Examples 4 to 7 (in which the oxidized glutathione solution having an oxidized glutathione concentration of 50 mg/L to 1000 mg/L was sprayed to shoots) was high, i.e., 72.7% to 84.1%, whereas a rooting rate of Comparative Example 2 (in which the oxidized glutathione solution was not sprayed to the shoots) was low, i.e., 56.8%.

Example 8

Oxidized glutathione was applied to a phylloplane of a cutting. That is, the cutting was prepared in the same way as that in Example 5, except that a mother tree of the cutting was *E. uro-grandis* (Line name: B). Then a base of the cutting was planted to the supporter similar to Example 5. An oxidized glutathione solution was prepared in the same way as Example 5, and, immediately after the base was planted, the oxidized glutathione solution was sprayed to the phylloplane in the form of a mist by use of a spray etc. A spray amount of the glutathione solution was set to about 1.1 ml per shoot. A breeding condition after planting the shoot was similar to Example 5, and a rooting rate was calculated in the same way as Example 5. The result is shown in Table 3.

Example 9

A seedling was bred in the same way as Example 8, except that a solution having an oxidized glutathione concentration of 500 mg/L was used as the oxidized glutathione solution. The result is shown in Table 3.

Example 10

A seedling was bred in the same way as Example 8, except that a solution having an oxidized glutathione concentration of 1000 mg/L was used as the oxidized glutathione solution. The result is shown in Table 3.

Comparative Example 3

A seedling was bred in the same way as Example 8, except that the oxidized glutathione solution was not sprayed to a phylloplane. The result is shown in Table 3.

TABLE 3

| | Variety name | Sprayed oxidized glutathione concentration (mg/L) | How to provide glutathione | Number of test pieces of shoot | Number of rooted shoots | Rooting rate (%) |
|---|---|---|---|---|---|---|
| Example 8 | E. uro-grandis B | 200 | sprayed to phylloplane | 88 | 48 | 54.5 |
| Example 9 | E. uro-grandis B | 500 | sprayed to phylloplane | 88 | 52 | 59.1 |
| Example 10 | E. uro-grandis B | 1000 | sprayed to phylloplane | 88 | 53 | 60.2 |
| Comparative Example 3 | E. uro-grandis B | 0 | — | 88 | 38 | 43.2 |

As is clearly from Table 3, a rooting rate of each of Example 8 to 10 (in which the oxidized glutathione solution of 200 mg/L to 1000 mg/L was sprayed to the phylloplane of the shoot) was high, i.e., 54.5% to 60.2%, whereas a rooting rate of Comparative Example 3 (in which the oxidized glutathione solution was not sprayed to the phylloplane) was low, i.e., 43.2%.

Example 11

A mango (*Mangifera Indica Linn*. variety name: Irwin) was used as a material of a cutting. Specifically, a cutting including one to three joints and one to five leaves was cut from a branch of a mother tree, and each leaf was partially cut off. Furthermore, the material was wounded by a cutter. The cutting was thus prepared.

The shoot thus obtained was washed with running water over night, and was dipped into an insecticide solution such as "Kotetsu". Then the shoot had been planted to a supporter infiltrated with a four-diluted MS medium (Composition: ammonium nitrate of 412.5 mg/L, potassium nitrate of 475 mg/L, sodium dihydrogenphosphate of 42.52 mg/L, potassium iodide of 0.21 mg/L, etc. Note that a carbon source other than glutathione was not added to this medium.) to which the oxidized glutathione of 50 mg/L, STS ($AgS_4O_6$) of 5 µM serving as a silver ion source, ascorbic acid of 50 mg/L serving an antioxidant, and IBA of 10 mg/L serving as a plant hormone were added. In this case, natural soil such as sand and akadama soil; or a composite soil of vermiculite, perlite, peat moss, etc. was used as the supporter. After this planting, the shoot was cultured for one and half months in carbon dioxide gas concentration of 1000 ppm at a temperature of 25° C. and a humidity of 60% under irradiation of red light having photosynthesis photon flux density of 51.3 µmol/m$^2$/S having a wavelength component of 650 nm to 670 nm to a wavelength component of 450 nm to 470 nm at a ratio of 8.2:1.8.

The culturing was carried out with a rectangular container (maximum size of about 20 cm to 22 cm in length×33 cm to 37 cm in width×15 cm to 17 cm in height) having a shape whose bulge was slightly protruded. A top surface of the culture container had ten circular openings which are covered with a polytetra-fluoroethylene film (Manufactured by Millipore Corporation, Product name: Milli-Seal) having a pore size of 0.45 µm. A carbon dioxide gas concentration inside the culture container was adjusted by a film covering the openings. Carbon dioxide gas outside the culture container was allowed to enter the culture container through this carbon dioxide gas permeable membrane covering the opening. Accordingly, a carbon dioxide gas concentration inside the culture container was about 1000 ppm due to the permeation of the carbon dioxide gas through the film covering the opening of the culture container. The culture container was irradiated with red light by use of a light irradiation device (Product name: CCFL unit, maker's name: Nippon Medical & Chemical Instruments CO., LTD.). Further, humidity in the culture container was about 100% by sealing the culture container with Parafilm.

Ten to twenty shoots were planted per culture container. A rooting rate was calculated from the number of test pieces of the shoot and the number of shoots (the number of rooted shoots) which had been rooted after the foliage was cultured for one and half months. The result is shown in Table 4.

Comparative Example 4

The culture was carried out in the same way as Example 11, except that oxidized glutathione was not added. The result is shown in Table 4.

TABLE 4

| | Variety name | Sprayed oxidized glutathione concentration (mg/L) | How to provide glutathione | Number of test pieces of shoot | Number of rooted shoots | Rooting rate (%) |
|---|---|---|---|---|---|---|
| Example 11 | Mango | 50 | adding glutathione to rooting medium | 26 | 7 | 266.9 |
| Comparative Example 4 | Mango | 0 | — | 26 | 5 | 19.2 |

As is clearly from Table 4, a rooting rate of Example 11 (in which oxidized glutathione of 50 mg/L was added to the medium) was 26.9%, whereas a rooting rate of Comparative Example 4 (in which oxidized glutathione was not added) was low, i.e., 19.2%.

Example 12

Oxidized glutathione was prepared in such a way that 1% granule oxidized glutathione was mixed with a composite soil was used. Specifically, 1% granule oxidized glutathione of 15 g was mixed with a composite soil of peat moss and vermiculite (5.5 L), and was then put into a seedling pot (3 cm in inner diameter×15 cm in height×66 holes). This seedling pot served as a supporter. A four-diluted MS medium (Composition: ammonium nitrate of 412.5 mg/L, potassium nitrate of 475 mg/L, sodium dihydrogenphosphate of 42.52 mg/L, and potassium iodide of 0.21 mg/L. Note that a carbon source was not added to this medium.) to which IBA serving as a plant hormone of 10 mg/L was added was sprayed from the above the seedling pot by use of a watering can so that the supporter was soaked with the four-diluted MS medium.

Tea plant was used as a material for a cutting. Specifically, a cutting grown to have a length of about 5 cm to 20 cm, about one to three joints, about one to six leaves was cut out from a mother tree, and a tip of each leaf was cut off. In this way, the cutting was adjusted and prepared.

A base of the cutting thus adjusted and prepared was planted to a supporter (66 cuttings were planted per seedling pot). After this planting, the shoot was cultured for one and half months in a carbon dioxide gas concentration of 1000 ppm, a temperature of 25° C., and a humidity of 60% having a wavelength component of 650 nm to 670 nm to a wavelength component of 450 nm to 470 nm at a ratio of 8.2:1.8 under irradiation of red light having photosynthesis photon flux density of 51.3 µmol/m$^2$/S. After that, the seedling pot was moved to a green house, and was bred for two and half months. In the green house, a high humidity (80% or more) was kept by frequently spraying mist. After two and half month from this moving, a rooting rate was calculated from the number of rooted cuttings. The result is shown in Table 5.

Example 13

The culture was carried out in the same way as Example 12, except that an amount of 1% granule oxidized glutathione to be added to a composite soil (5.5 L) was set to 75 g. The result is shown in Table 5.

Comparative Example 5

The culture was carried out in the same way as Example 12, except that 1% granule oxidized glutathione was not added to the medium. The result is shown in Table 5.

TABLE 5

| | Variety name | Oxidized glutathione concentration in composite soil (mg/L) | How to provide glutathione | Number of test pieces of shoot | Number of rooted shoots | Rooting rate (%) |
|---|---|---|---|---|---|---|
| Example 12 | Tea plant | 3 | mix with soil | 462 | 443 | 96.0 |
| Example 13 | Tea plant | 15 | mix with soil | 462 | 461 | 99.6 |
| Comparative Example 5 | Tea plant | 0 | — | 462 | 289 | 62.1 |

As is clearly from Table 5, a rooting rate of each of Examples 11 and 12 (in which granule oxidized glutathione was mixed with a composite soil so that an oxidized glutathione concentration was 3 mg/L to 15 mg/L), was high, i.e., 96.0% to 99.6%, whereas a rooting rate of Comparative Example 5 (in which granule oxidized glutathione was not mixed) was low, i.e., 62.1%.

Example 14

The culture was carried out in the same way as Example 1, except that genetically modified *E. globulus* (Line name: Clone B) was used and a base of the shoot was wounded by a pair of scissors. Note that the base of the shoot (the aforementioned cross-sectional surface) was cut in two directions orthogonal to each other by use of a pair of scissors, and therefore the base was wounded so as to have a cross-shaped wound seen from a front direction. The result is shown in Table 6.

Example 15

The culture was carried out in the same way as Example 14, except that an amount of oxidized glutathione to be added to the medium was set to 75 mg/L. The result is shown in Table 6.

Comparative Example 6

The culture was carried out in the same way as Example 14, except that oxidized glutathione was not added. The result is shown in Table 6.

TABLE 6

| | Line name | Oxidized glutathione concentration in medium (mg/L) | Number of test pieces of shoot | Number of rooted shoots | Rooting rate (%) |
|---|---|---|---|---|---|
| Example 14 | *E. globulus* (Clone B) | 25 | 9 | 8 | 88.9 |
| Example 15 | *E. globulus* (Clone B) | 75 | 9 | 7 | 77.8 |
| Comparative Example 6 | *E. globulus* (Clone B) | 0 | 27 | 6 | 22.2 |

As is clearly from Table 6, a rooting rate of each of Examples 14 and 15 (in which oxidized glutathione of 25 mg/L to 75 mg/L was added to the medium) was high, i.e., 77.8% to 88.9%, whereas a rooting rate of Comparative Example 5 (in which oxidized glutathione was not added) was low, i.e., 22.2%.

Example 16

The culture was carried out in the same way as Example 1, except that (i) a shoot of genetically modified *E. globulus* (Line name: Clone C) was used, (ii) an amount of oxidized glutathione to be added to a medium was set to 50 mg/L, and (iii) a base of the shoot was wounded by a pair of scissors.

Example 17

The culture was carried out in the same way as Example 16, except that a shoot of genetically modified *E. globulus* (Line name: Clone D) was used. The result is shown in Table 7.

Example 18

The culture was carried out in the same way as Example 16, except that a shoot of genetically modified *E. globulus* (Line name: Clone E) was used. The result is shown in Table 7.

Example 19

The culture was carried out in the same way as Example 16, except that a shoot of *E. globulus* (wild type F) was used. The result is shown in Table 7.

Comparative Example 7

The culture was carried out in the same way as Example 16, except that oxidized glutathione was not added. The result is shown as Table 7.

Comparative Example 8

The culture was carried out in the same way as Example 17, except that oxidized glutathione was not added. The result is shown as Table 7.

Comparative Example 9

The culture was carried out in the same way as Example 18, except that oxidized glutathione was not added. The result is shown as Table 7.

Comparative Example 10

The culture was carried out in the same way as Example 19, except that oxidized glutathione was not added. The result is shown as Table 7.

TABLE 7

|  | Line name | Oxidized glutathione concentration in medium (mg/L) | Number of test pieces of shoot | Number of rooted shoots | Rooting rate (%) |
|---|---|---|---|---|---|
| Example 16 | E. globulus (Clone C) | 50 | 27 | 26 | 96.3 |
| Example 17 | E. globulus (Clone D) | 50 | 18 | 16 | 88.9 |
| Example 18 | E. globulus (Clone E) | 50 | 27 | 24 | 88.9 |
| Example 19 | E. globulus (wild-type F) | 50 | 18 | 18 | 100.0 |
| Comparative Example 7 | E. globulus (Clone C) | 0 | 72 | 49 | 53.1 |
| Comparative Example 8 | E. globulus (Clone D) | 0 | 50 | 9 | 18.0 |
| Comparative Example 9 | E. globulus (Clone E) | 0 | 55 | 17 | 30.9 |
| Comparative Example 10 | E. globulus (wild-type F) | 0 | 18 | 2 | 11.1 |

As is clearly from Table 7, a rooting rate of each of Examples 16 to 19 (in which oxidized glutathione of 50 mg/L was added to the medium) was high, i.e., 88.9% to 100%, whereas a rooting rate of each of Comparative Examples 7 to 10 (in which oxidized glutathione was not added) was low, i.e., 11.1% to 53.1%.

Example 20

The culture was carried out in the same way as Example 16, except that genetically modified E. globulus (Line name: Clone G) whose rooting is clearly extremely difficult was used as a material. The result is shown in Table 8.

Example 21

The culture was carried out in the same way as Example 16, except that genetically modified E. globulus (Line name: Clone H) whose rooting is clearly extremely difficult was used as the material. The result is shown in Table 8.

Example 22

The culture was carried out in the same way as Example 16, except that genetically modified E. globulus (Line name: Clone I) whose rooting is clearly extremely difficult was used as the material. The result is shown in Table 8.

Comparative Example 11

The culture was carried out in the same way as Example 20, except that (i) oxidized glutathione was not added and (ii) the base of the shoot was not wounded. The result is shown in Table 8.

Comparative Example 12

The culture was carried out in the same way as Example 21, except that (i) oxidized glutathione was not added and (ii) the base of the shoot was not wounded. The result is shown in Table 8.

Comparative Example 13

The culture was carried out in the same way as Example 22, except that (i) oxidized glutathione was not added and (ii) the base of the shoot was not wounded. The result is shown in Table 8.

TABLE 8

|  | Line name | Oxidized glutathione concentration in medium (mg/L) | Number of test pieces of shoot | Number of rooted shoots | Rooting rate (%) |
|---|---|---|---|---|---|
| Example 20 | E. globulus (Clone G) | 50 | 18 | 6 | 33.3 |
| Example 21 | E. globulus (Clone H) | 50 | 5 | 2 | 40.0 |
| Example 22 | E. globulus (Clone I) | 50 | 5 | 1 | 20.0 |
| Comparative Example 11 | E. globulus (Clone G) | 0 | 18 | 0 | 0.0 |
| Comparative Example 12 | E. globulus (Clone H) | 0 | 9 | 0 | 0.0 |
| Comparative Example 13 | E. globulus (Clone I) | 0 | 45 | 0 | 0.0 |

As is clearly from Table 8, none of the shoots is rooted in Comparative Examples 11 to 13 (in which oxidized glutathione was not added and the base of the shoot was not wounded), whereas a rooting rate of each of Examples 20 to 22 (in which oxidized glutathione of 50 mg/L was not added to the medium) was high, i.e., 20.0% to 40.0%.

The invention being thus described, it will be obvious that the same way may be varied in many ways. Such variations are not to be regarded as a departure from the spirit and scope of the invention, and all such modifications as would be obvious to one skilled in the art are intended to be included within the scope of the following claims.

INDUSTRIAL APPLICABILITY

The present invention makes it possible to rapidly produce a large amount of clone seedlings from shoots of the plant, and it is desired that the shoot of the plants be industrially used.

The invention claimed is:

1. A method for producing a clone seedling, comprising
cultivating a shoot of a plant under the presence of oxidized glutathione and the absence of auxin;
checking whether or not the shoot of the plant thus cultivated is rooted; and
selecting the shoot of the plant thus rooted.

2. The method as set forth in claim 1, wherein the step of cultivating is carried out by use of a medium containing oxidized glutathione.

3. The method as set forth in claim 2, wherein a oxidized glutathione concentration in the medium is within the range from 1 mg/L to 5000 mg/L.

4. The method as set forth in claim 2, wherein the medium does not contain a carbon source other than oxidized glutathione.

5. The method as set forth in claim 1, wherein the step of cultivating is carried out by contacting a solution containing oxidized glutathione with a the shoot of the plant.

6. The method as set forth in claim 5, wherein a oxidized glutathione concentration in the solution is within the range from 1 mg/L to 5000 mg/L.

7. The method as set forth in claim 1, wherein the plant is a plant which is a difficult-to-root species.

8. The method as set forth in claim 7, wherein the plant is a eucalyptus plant.

9. The method as set forth in claim 1, wherein the step of cultivating is carried out under irradiation of light having a wavelength component of 650 nm to 670 nm to a wavelength component of 450 nm to 470 nm at a ratio of 9:1 to 7:3.

10. The method as set forth in claim 1, wherein the step of cultivating is carried out under carbon dioxide gas supply.

11. The method as set forth in claim 10, wherein a supplying amount of the carbon dioxide gas is within the range from 300 ppm to 2000 ppm.

12. The method as set forth in claim 1, wherein the step of cultivating is carried out under a humidity of 80% or more.

13. The method as set forth in claim 1, wherein the shoot used has a base wounded.

14. The method as set forth in claim 1, wherein the shoot is any one of (i) a cutting, (ii) a multiple shoot which is obtained by culturing an organ under a sterile condition, wherein the organ is collected from a mother plant, and (iii) a foliage which is obtained by culturing the organ under a sterile condition.

15. The method as set forth in claim 3, wherein the oxidized glutathione concentration is within the range from 1 mg/L to 100 mg/L.

* * * * *